United States Patent
Davies et al.

(10) Patent No.: US 9,422,516 B2
(45) Date of Patent: Aug. 23, 2016

(54) BIOREACTOR CHAMBER

(75) Inventors: David Davies, Crewe (GB); Paul Gordon, Sheffield (GB); John Malcolm Wilkinson, Chesterfield (GB); William Ward, Sheffield (GB)

(73) Assignee: Parker-Hannifin Manufacturing Limited, South Yorkshire (GB)

( * ) Notice: Subject to any disclaimer, the term of this patent is extended or adjusted under 35 U.S.C. 154(b) by 197 days.

(21) Appl. No.: 14/118,281

(22) PCT Filed: May 3, 2012

(86) PCT No.: PCT/GB2012/050960
§ 371 (c)(1),
(2), (4) Date: Jan. 17, 2014

(87) PCT Pub. No.: WO2012/156682
PCT Pub. Date: Nov. 22, 2012

(65) Prior Publication Data
US 2014/0127799 A1    May 8, 2014

(30) Foreign Application Priority Data

May 16, 2011 (GB) .................................. 1108165.0
Jul. 12, 2011 (GB) .................................. 1111898.1
Dec. 23, 2011 (GB) .................................. 1122254.4

(51) Int. Cl.
*C12M 1/00* (2006.01)
*C12M 3/00* (2006.01)

(52) U.S. Cl.
CPC ............... *C12M 23/02* (2013.01); *C12M 23/38* (2013.01); *C12M 23/46* (2013.01); *C12M 23/48* (2013.01)

(58) Field of Classification Search
CPC ...... C12M 23/02; C12M 23/38; C12M 23/46; C12M 23/48
USPC .................................................. 435/289.1
See application file for complete search history.

(56) References Cited

U.S. PATENT DOCUMENTS

| 3,704,802 | A | 12/1972 | Schultz | |
| 5,414,556 | A * | 5/1995 | Focht | 359/398 |
| 7,022,518 | B1 * | 4/2006 | Feye | C12M 23/08 435/297.1 |
| 2003/0215940 | A1 * | 11/2003 | Lacey et al. | 435/305.2 |
| 2005/0176155 | A1 * | 8/2005 | Klein et al. | 436/163 |

FOREIGN PATENT DOCUMENTS

| EP | 2031501 | 3/2009 |
| GB | 2470227 | 11/2010 |

(Continued)

OTHER PUBLICATIONS

International Search Report for corresponding Patent Application No. PCT/GB2012/050901 dated Jul. 11, 2012.

(Continued)

*Primary Examiner* — Nathan Bowers
*Assistant Examiner* — Timothy Barlow
(74) *Attorney, Agent, or Firm* — Renner, Otto, Boisselle & Sklar, LLP

(57) ABSTRACT

A bioreactor chamber assembly comprising a cap and a base capable of being coupled together axially to define an internal chamber. The cap and base comprise interengaging formations that are coupled together by a twist-lock rotation of the base and cap to provide a fluid tight seal between the base and cap via respective sealing surfaces.

19 Claims, 12 Drawing Sheets

(56) References Cited

FOREIGN PATENT DOCUMENTS

| WO | 88/01605 | 3/1998 |
| WO | 2005/123258 | 12/2005 |
| WO | 2010/040699 | 1/2010 |
| WO | 2010/013068 | 2/2010 |

OTHER PUBLICATIONS

International Preliminary Report on Patentability for corresponding Patent Application No. PCT/GB2012/050960 dated Aug. 16, 2013.

* cited by examiner

A - A

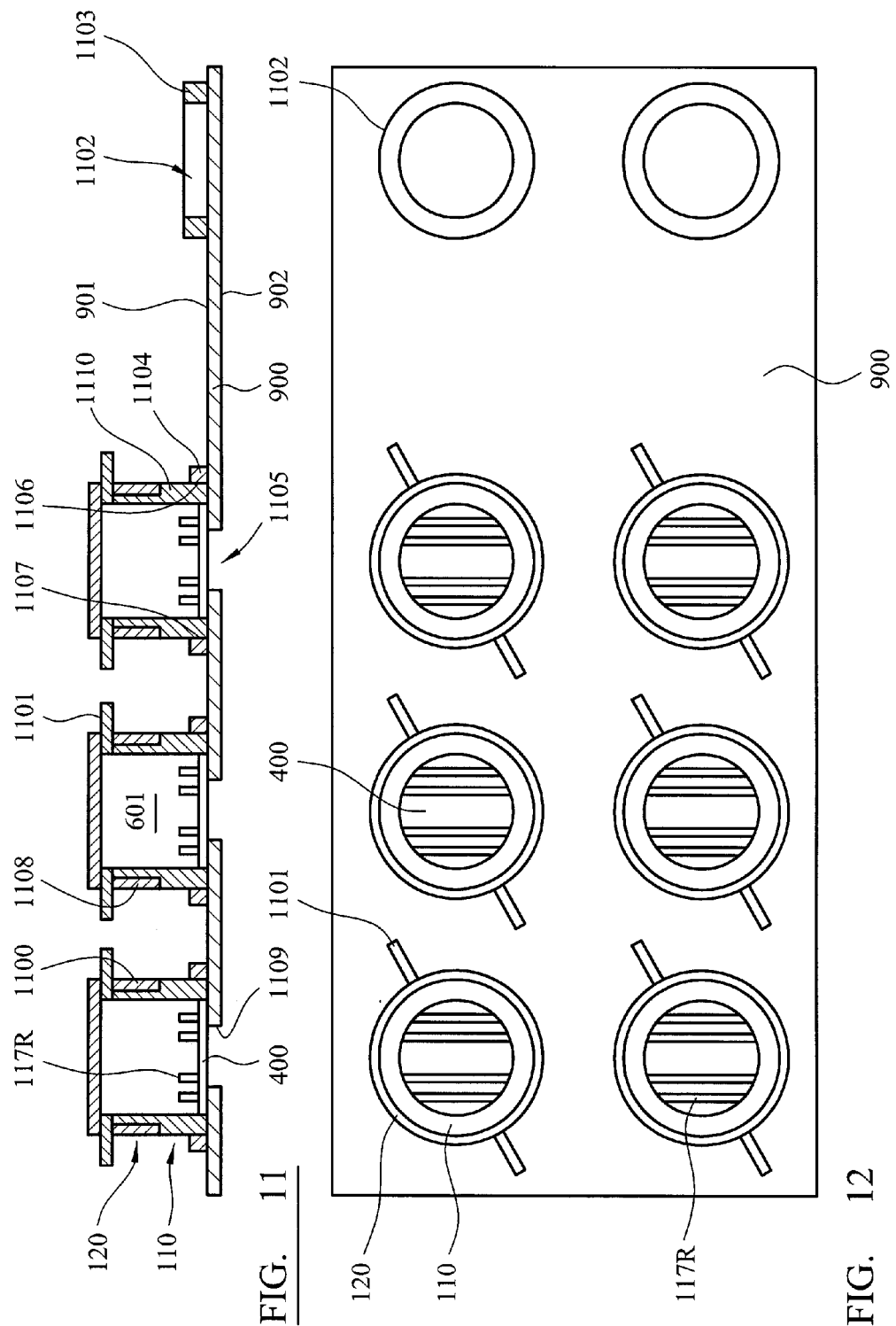

BIOREACTOR CHAMBER

This application is a national phase of International Application No. PCT/GB2012/050960 filed May 3, 2012 and published in the English language, which claims priority to GB 1108165.0 filed May 16, 2011, GB 1111898.1 filed Jul. 12, 2011, and GB 1122254.4 filed Dec. 23, 2011, which are hereby incorporated herein by reference.

The present invention relates to a bioreactor chamber assembly and in particular, although not exclusively, to a chamber assembly having a base and a cap that are releasably coupled together via interengaging formations provided at the base and cap.

In vitro cell culturing is becoming increasingly important in pharmacology, physiology and toxicology research. Currently, a wide range of biological materials are cultured and studied in vitro including for example monolayer cell cultures, scaffold cultures, tissue slices etc.

It is conventionally understood that biological tissue, during growth in vivo, is subject to physical and chemical stimuli that, to varying degree, affect the pathological and physiological status which in turn affects the development and resulting function of the tissue. Accordingly, a number of different types of systems have been developed with the capability of reproducing, as closely as possible, those environmental conditions experienced by in vivo proliferating cells. Example bioreactors for cell culturing in vitro are described in WO 2010/013068; WO 2010/040699; WO 2005/123258 and GB 2470227.

Typically, these bioreactors comprise a single or an array of internal chambers within which the cells are grown. To simulate the in vivo conditions, means are typically provided to allow a through flow of a culture medium within the chamber. This typically involves one or more fluid inlet and outlet ports connecting the chamber interior to a fluid network or circuit for culture medium circulation. However, sample preparation and dynamic testing typically involves assembly, disconnection and reassembly of the bioreactor chamber components. The connection and assembly is currently burdensome due largely to the interengagement mechanism of the various components. Currently, the time taken for assembly is too long and the reliability of creating a fluid tight seal at the chamber interior cannot be guaranteed.

There is therefore a need for a bioreactor chamber assembly that addresses the above problem.

Accordingly, the inventors provide a bioreactor chamber assembly having a convenient releasable interlocking connection mechanism to couple the bioreactor components quickly and conveniently whilst providing a reliable fluid tight seal about the chamber interior. This is achieved, in part, by constructing the chamber assembly from a base and cap, with each component comprising respective interengaging formations that provide a releasable lock arrangement via a twist-lock rotation of the base and/or the cap.

The fluid tight seal is provided by one or more respective sealing surfaces at the base and cap that couple together preferably by an interference or friction fit arrangement such that a strength of the fluid tight seal is increased as the cap and base are drawn together in an axial direction relative to a longitudinal axis bisecting both components. The 'drawing together' of the base and cap is provided, according to one embodiment, by tapered flanges that form a component part of the interengaging formations. These flanges are configured to abut one another over an inclined abutment surface so as to compress both the cap and base together axially during coupling via the twist-lock rotation assembly.

According to a first aspect of the present invention that is provided a bioreactor chamber assembly comprising: a base and a cap configured to be coupled together to define an internal chamber; the base and cap each comprising respective interengaging formations to allow the base and cap to be realisably coupled together axially relative to a longitudinal axis bisecting the base and cap by a twist-lock rotation of at least one of the base and cap about the longitudinal axis; the base and cap each comprising a respective sealing surface that mate together to provide a fluid tight seal when the base and cap are coupled together.

Preferably, the respective interengaging formations project radially outward from at least one of the base and cap. Preferably, the respective interengaging formations are spaced apart circumferentially around the base and cap.

Preferably, the respective interengaging formations each comprise a flange portion extending in a circumferential direction around the base and cap wherein respective flange portions of the base and cap are configured to slide over one another to couple the base and cap together and prevent axial separation. Preferably, each flange of the base and cap comprises a respective abutment surfaces extending in the circumferential direction around the longitudinal axis and configured to cooperatively abut one another when the base and cap are coupled together by rotation about the longitudinal axis; wherein at least one of the abutment surfaces extends in a circumferential direction at an angle transverse to a plane perpendicular to the longitudinal axis such that as the flanges of the base and cap are slid over one another the base and cap are drawn together axially.

Optionally, at least one of the sealing surfaces extends in the direction of the longitudinal axis and is tapered to extend transverse to the longitudinal axis so as to provide an interference or friction fit arrangement with the corresponding sealing surface of the alternate base or cap. This has the advantage that a distribution of force at the mated sealing surfaces between the first (base) and second (cap) components around the chamber may be made more uniform to increase the seal strength. Preferably, at least one of the sealing surfaces of the base and cap comprises a ridged portion extending circumferentially around the internal chamber to abut against a portion of the sealing surface of the alternate base or cap to provide a fluid tight seal.

Preferably, the interengaging formations of the base and cap are formed integrally with the respective base and cap. In order to allow passage or circulation of a fluid culture medium through the internal chamber, the cap comprises a fluid inlet aperture and a fluid outlet aperture. Preferably, the inlet and outlet are positioned diametrically opposed to one another. Optionally, the inlet and outlet are positioned at the lid at the same axial position relative to the longitudinal axis. Alternatively, the inlet and outlet maybe positioned at different positions along the longitudinal axis bisecting the base and lid.

Preferably, at least one of the cap and base comprise side walls that extend in the direction of the longitudinal axis that define a part of the internal chamber. Preferably, both the cap and base comprise side walls that extend in a direction of the longitudinal axis. Alternatively, an intermediate body (hollow) may be positioned between he base and cap and comprise side walls to define, in part, the chamber interior, with the chamber ends defined by the base and cap. The same or similar interengaging formation may be provided at the intermediate body so as to allow convenient and reliable quick assembly as described.

Preferably, at least a portion of at least one of the base and cap comprises a resilient deformable material. Preferably, the resilient deformable material comprises silicone. Optionally, the base and cap comprise predominantly silicone. Advantageously at least one of the sealing surfaces of the components comprises the resiliently flexible material. Optionally, the first and/or second component may each be formed from a silicone, a silicone rubber or silicone based material, for example by injection moulding, casting or any other suitable method of manufacture. The resiliently flexible material may have a hardness in the range of from around 10 Shore A to around 100 Shore A, optionally from around 10 Shore A to around 90 Shore A. The Shore A hardness scale is defined in ASTM D2240 as type A. In some embodiments the Shore A hardness is in the range of one selected from amongst 1 to 10, 11 to 20, 21 to 30 31 to 40, 41 to 50, 51 to 60, 61 to 70, 71 to 80, 81 to 90, 91 to 100 Shore A. Other hardness values are also useful. Other materials are also useful such as thermoplastics materials, elastomeric materials, metallic materials or any other suitable biocompatible material.

The base and/or cap component may be formed from one material and provided with a layer or sheath of a second material having a lower hardness. For example, the first (base) and/or second (cap) component may have a first portion in the form of a core, a former or other part formed from a metallic or plastics material, and a second portion coupled to the first portion. The second portion may comprise the resiliently flexible material described above. Optionally, the base and cap are formed from different materials of different respective hardness.

Optionally, the base comprises a transparent window non-integrally formed with the base. Optionally, the base comprises a receiving socket extending around an aperture at an end region of the base, the window partially received by the socket to retain the window at the base. Optionally, the cap comprises a transparent window integrally formed with the cap.

Alternatively, the cap comprises a transparent window non-integrally formed with the cap. Preferably, the window forms a region of the roof of the cap. Preferably, the window is inclined at an angle relative to a plane perpendicular to a longitudinal axis bisecting the assembly. Preferably, the window comprises a substantially uniform thickness.

According to a second aspect of the present invention that is provided bioreactor apparatus comprising: a plurality of bioreactor chamber assemblies as described herein; and a support structure mounting the plurality of the bioreactor chamber assemblies in substantially fixed position at the support structure, the support structure comprising a plurality of respective mounts to releasably mount each bioreactor chamber assembly at the support structure via the base of each bioreactor chamber assembly.

Preferably, the support structure comprises a plurality of apertures, each aperture provided at a region of each respective mount such that each respective aperture is positioned below a respective bioreactor chamber assembly when mounted at the support structure. Optionally, the mount comprises at least one shoulder extending upwardly from the support structure to abut against an outer surface of each respective base.

The present bioreactor chamber assembly can be assembled in a relatively rapid manner and with a reliable, fluid-tight seal formed between the first and second components. Rapid and reliable assembly can be vital, for example when performing experiments on live tissue specimens that are sensitive to their environment. For example it may be inadvisable to allow a tissue sample to experience a large excursion of one or more parameters such as a temperature or environmental humidity to which the tissue is exposed. Similarly, it may be inadvisable for a specimen to be removed from a liquid medium environment for longer than a prescribed period of time, which may be relatively short. Such situations can easily arise when a tissue is transferred from one environment into the assembly, for example from a body of a human or animal into the assembly. Accordingly, embodiments of the present invention allow tissue samples to be transferred into and sealed within a bioreactor assembly in a more rapid and reliable manner than known bioreactors.

Furthermore, the fact that the assembly comprises a twist-lock coupling reduces the risk that the first and second components become separated unintentionally. For example, if a pressure of gas or liquid in the chamber rises to a relatively high level unexpectedly or inadvertently the risk that the first and second components become separated is reduced. Furthermore a bioreactor chamber assembly according to an embodiment of the present invention may be arranged to be used in experiments or applications in which relatively high internal fluid pressures are required to be established.

Advantageously the first component comprises a plurality of engaging flanges arranged to respectively receive or overlap in the axial direction with a corresponding plurality of engaging flanges of the second component. This has the advantage that a distribution of force around the interface between the first and second components may be made more uniform and unintentional axial separation is prevented.

Optionally, the sealing surfaces of the first and second components may be arranged to be provided in juxtaposition with one another when the first and second components are coupled together thereby to form the fluid tight seal. Optionally, both of the sealing surfaces may comprise a taper, the surfaces being tapered in a complementary manner. The provision of tapered portions enables a hygienic fluid-tight seal to be formed in a rapid and reliable manner without possible areas of entrapment.

Furthermore, provision of one or more tapered mating surfaces and a ridged portion in addition has the advantage of further reducing a risk of leakage of fluid into or out from the bioreactor chamber internal environment.

Optionally, the complementary interengaging formations of the first and second components may comprise a detente. Thus one component may comprise a protrusion such as a ridged portion and the other may comprise a corresponding recessed portion. Accordingly, in some arrangements the flange portion of the respective first and second components comprise a detente. The base and cap components may comprise 2, 3, 4, 5, 6, 7, 8, 9, 10 or any other suitable number of corresponding flange portions.

The second component may comprise a cap portion defining an end wall of the chamber. The cap portion may comprise a support portion for supporting a sample. The support portion may comprise a ridged portion. The cap portion may be arranged to support the bioreactor on a surface such as a benchtop.

The feature of a ridged portion has the advantage that when a sample is placed on the support the surface of the sample facing the support may be exposed to fluid in the portions between ridges.

In a further aspect of the invention there is provided a method of releasably coupling first and second components of a bioreactor chamber assembly together to define an internal volume of the chamber, the method comprising bringing respective complementary interengaging formations of the components together and coupling the components together by means of the interengaging formations in a twist-lock operation to form a fluid tight seal, the twist-lock operation comprising the step of receiving by means of at least one flange portion of the first component at least one flange portion of the second component.

Preferably, the bioreactor chamber assembly comprises: a chamber portion; liquid inlet aperture to allow fluid to flow into the chamber portion; a liquid outlet aperture to allow fluid to flow out from the chamber portion, the liquid inlet and liquid outlet apertures being respective different apertures. Embodiments of the present invention allow flow of a liquid media through the chamber portion via the liquid inlet and outlet apertures to replenish nutrients required by biological material within the chamber assembly.

According to a further aspect of the present invention there is provided a bioreactor chamber assembly comprising: first and second components configured to be coupled to one another axially relative to a longitudinal axis bisecting the first and second components to define an internal chamber; the first and second components having respective mating portions each with a sealing surface extending in the longitudinal direction and surrounding the internal chamber wherein at least one of the sealing surfaces is tapered so as to extend transverse to the longitudinal axis to provide an interference or friction fit arrangement whereby a strength of a fluid tight seal between the respective sealing surfaces increases as the first and second components are coupled together axially; the first and second components comprising respective interangaging formations configured to engage one another when the first and second components are coupled to prevent axial separation of the first and second components.

Optionally, one of the first or second components, being the base component, comprises a transparent window formed non-integrally with the base component. Preferably, the base component comprises a recessed receiving socket extending around an aperture or through-bore provided in a lower region and surface of the base component. The socket and window are dimensioned accordingly such that the window is trapped and retained within the socket when positioned at the base to bridge or span the through-bore or aperture in the base component.

Optionally, a separate o-ring, gasket or seal is provided at the region of the socket and window to provide a fluid tight seal at the base component.

Optionally, a separate retainer body is releasably attachable to the base component and is configured to sit over and about a portion of the window to retain the window in position at the base component. Optionally, the retainer is held in position at the base component via mechanical interlocking means provided by screw threads, frictional mating surfaces, screw of push fit interconnections that allow the retainer to be releasably secured at a base or lower surface region of the base component. Preferably, the base component is formed from a resiliently deformable material and the non-integral window is retained in position within the recessed socket by suitable abutment shoulders extending radially inward from the base component towards the axial centre of through-bore or aperture extending through the base component.

According to a further aspect of the present invention there is provided bioreactor apparatus comprising: a plurality of base components each configured to form a respective bioreactor having an internal chamber when coupled to corresponding cap components; a plurality of cap components to releasably couple to the plurality of base components, the base and cap components having respective mating portions each with a sealing surface that when coupled together form a fluid tight seal at each respective internal chamber defined by the base and cap components; the base and cap components comprising respective interengaging formations configured to engage one another when the base and cap components are coupled together to prevent axial separation of the base and cap components; and a support structure connecting the plurality of base components in fixed position and formed integrally with each of the base components.

Preferably, the base components project upwardly from the support structure to define upstanding wells. Preferably, each base component comprises walls that define the internal chamber. Optionally, the support structure comprises three, four, five, six, eight, or ten base components. Preferably the support structure comprises a substantially linear plate-like body with the base components extending from one face of the plate-like body.

Preferably, the support structure comprises means to mount one or a plurality of fluid reservoirs that may be interconnected to the bioreactors mounted at the plate. Optionally, the support structure comprises attachment means to enable a plurality of support structures to be releasable attached together to form an array of support structures and bioreactors.

According to a further aspect of the present invention there is provided a bioreactor chamber assembly comprising a first and a second component arranged to define an internal chamber of the assembly, the first and second components being provided with complimentary and respective first and second interlocking formations whereby the first and second components may be releaseably coupled together to form a fluid type seal about the internal chamber; at least one of the first and second components comprising a sealing surface part surrounding the internal chamber, the sealing surface comprising a taper relative to a longitudinal axis bisecting the first and second components so as to provide an interference or friction fit arrangement between the first and second components as they are coupled together.

Optionally, the first and second interlocking formations of the two components (base and cap) comprise cooperating screw threads or the twist-lock formations as described herein. Alternatively, the first and second interlocking formations may be any type of two part locking mechanism such as bayonet, snap-click, push-fit, press-fit, tongue and groove or hook and barb type connections.

Advantageously both components may comprise a transparent thermoplastic material. This feature has the advantage that a hygienic fluid-tight seal may be formed in a reliable manner without possible areas of entrapment.

Preferably, the support structure comprises a plurality of apertures provided at the regions for attachment of each bioreactor. Preferably, a diameter or width of each aperture of the support structure is less than a diameter or width of the internal chamber of the bioreactor. Preferably, the attachment means comprises at least one shoulder extending upwardly from the support structure. Preferably, the attachment means comprises any one or a combination of a click-lock mechanism, a twist-lock mechanism, a bayonet arrangement, cooperating screw threads, a push-fit arrangement, a snap-lock arrangement or any friction fit releasable locking mechanism having a first part provided at a shoulder and a second part provided at each bioreactor.

Optionally, each attachment means comprises a ridge configured to frictionally engage a respective base component to releaseably attach each base component to the support structure. Preferably, each attachment means is a mount and comprises screw threads configured to engage with corporating screw threads formed on each base component. Alternatively, each mount and each base component comprises respective first and second halves of a screw type interlocking mechanism.

Preferably, the support structure comprises a plurality of apertures extending through the support structure from an upper to a lower surface. Preferably, the support structure further comprises a plurality of transparent windows extending over each aperture and partially defining the internal chamber of each bioreactor.

According to a further aspect of the present invention there is provided a method of creating and maintaining an environment to support a biological species, the method comprising: providing a chamber body having walls that define an internal chamber to accommodate the biological species; the chamber body comprising: a base and a cap configured to be coupled together to define the internal chamber; the base and cap each comprising respective interengaging formations to allow the base and cap to be realisably coupled together axially relative to a longitudinal axis bisecting the base and cap by rotation of at least one of the base and cap about the longitudinal axis; the base and cap each comprising a respective sealing surface that mate together to provide a fluid tight seal when the base and cap are coupled together; and providing a flow of a liquid through the internal chamber in contact with biological species via a liquid inlet and a liquid outlet at the chamber body.

The present method is configured to support the growth, culturing and development of biological tissue and the growth and in particular the proliferation of living cells. Preferably, the method further comprises maintaining and controlling the flow of the liquid through the internal chamber in contact with biological species by pumping the liquid from a liquid reservoir through the internal chamber using a pump and a suitable liquid conduit network coupled to the liquid inlet and liquid outlet.

Embodiments of the invention will now be described, by way of example only and with reference to the accompanying figures in which.

Figure 1A:
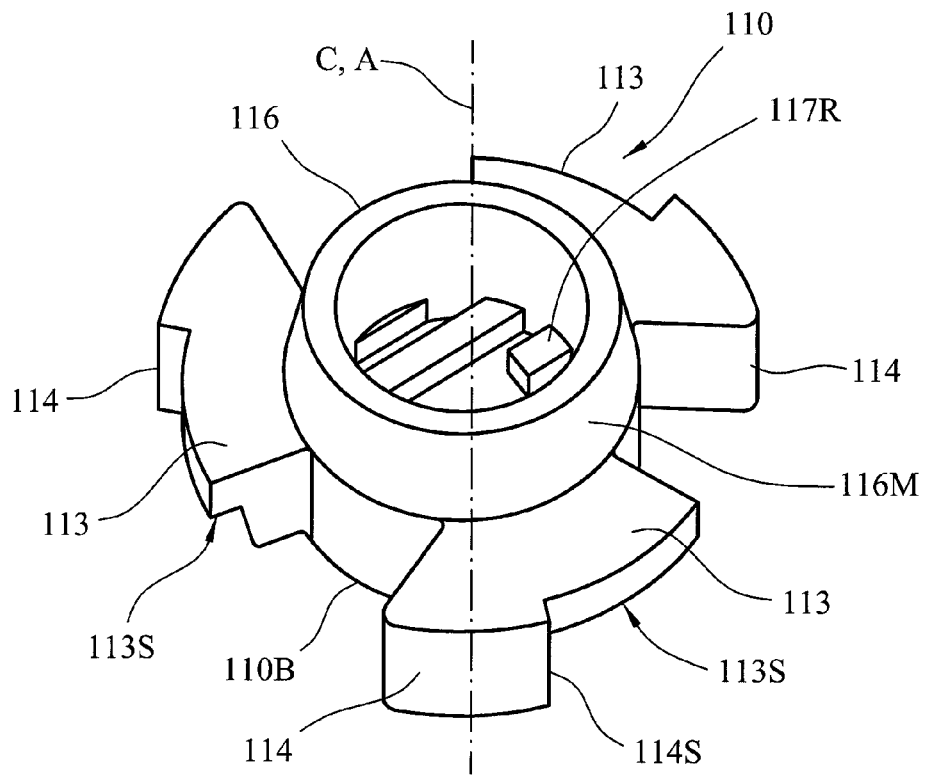
FIG. 1A is a perspective view from above of a base part of a bioreactor chamber according to a specific implementation of the present invention.
Figure 1B:
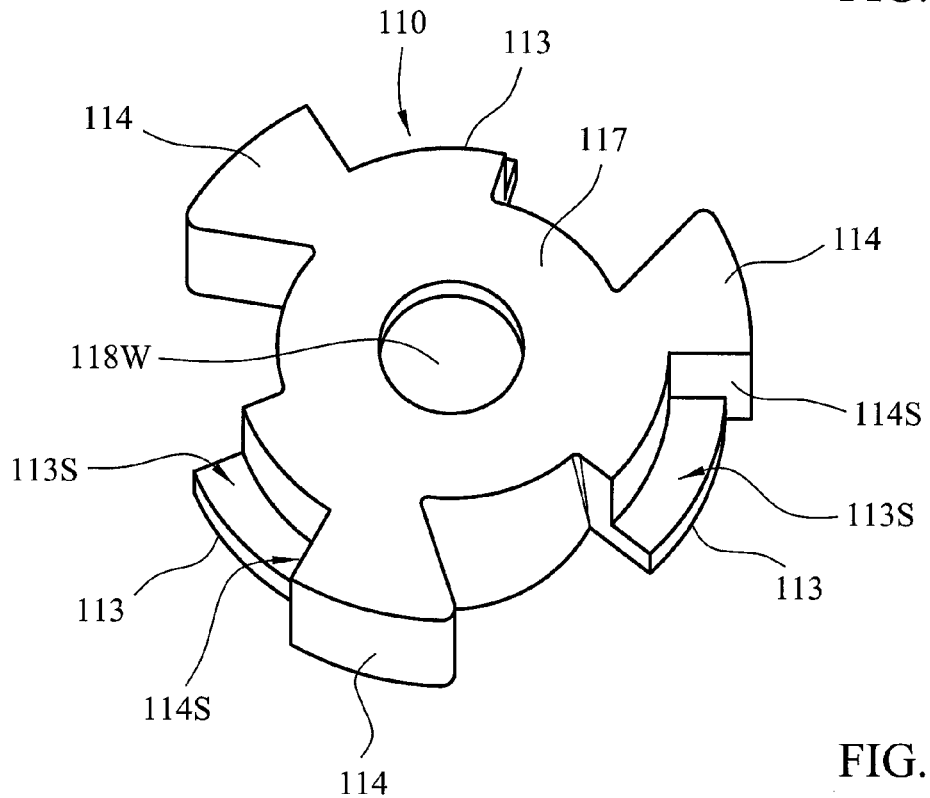
FIG. 1B is a perspective view from below of the bioreactor base of FIG. 1A.
Figure 1C:
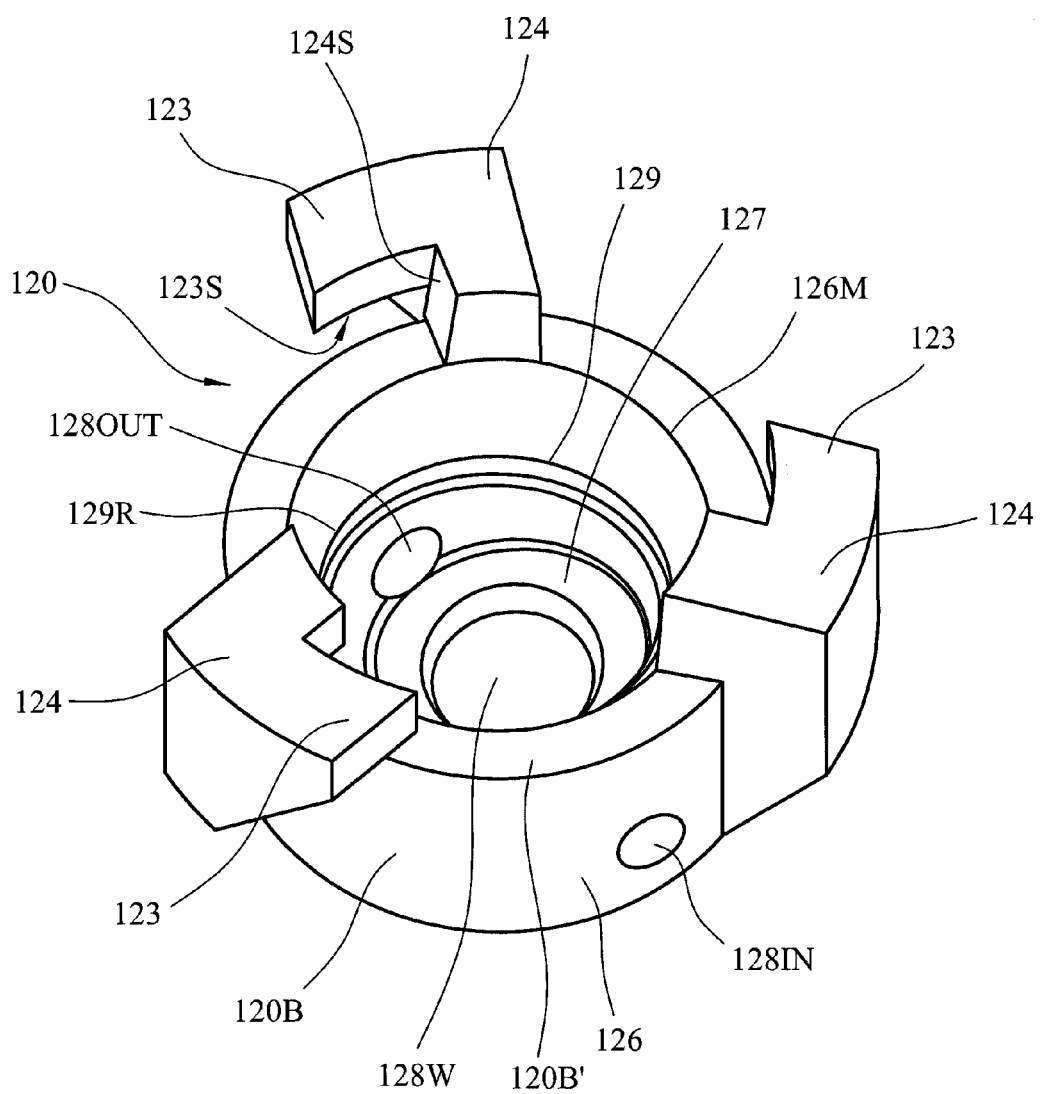
FIG. 1C is a perspective view from below of a cap part of a bioreactor chamber according to a specific implementation of the present invention.
Figure 2A:
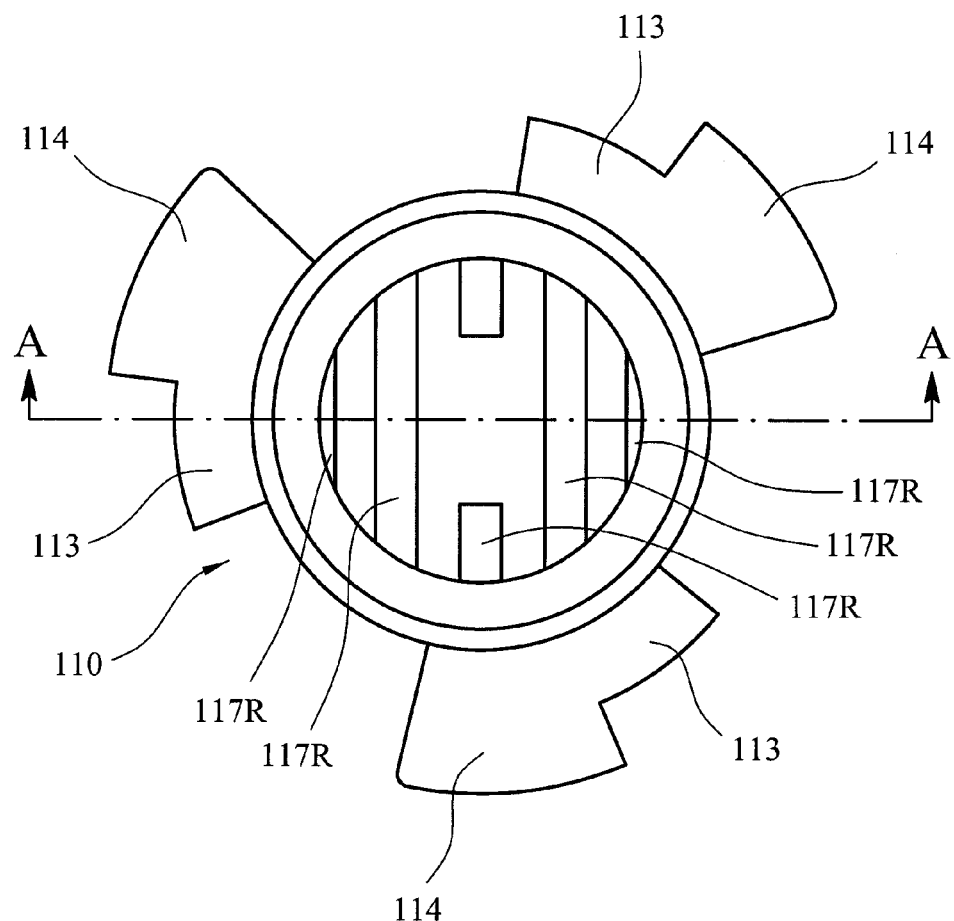
FIG. 2A is a plan view of the base of FIG. 1B.
Figure 2B:
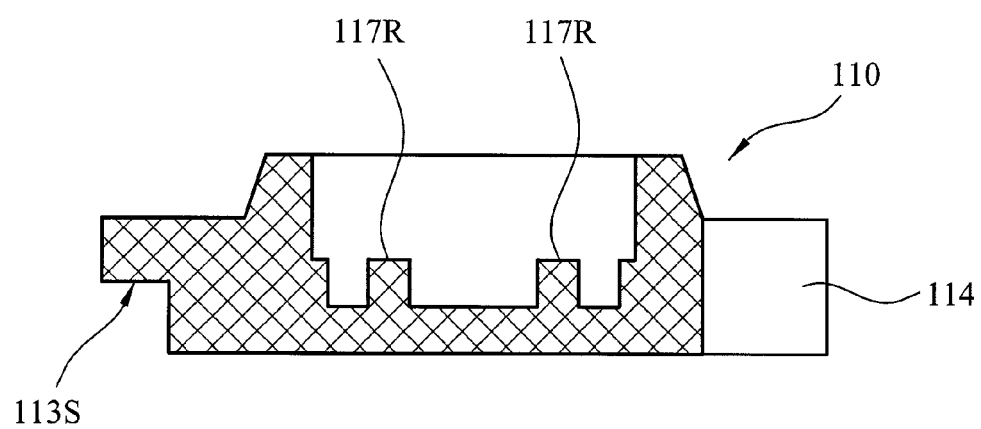
Figure 2C:
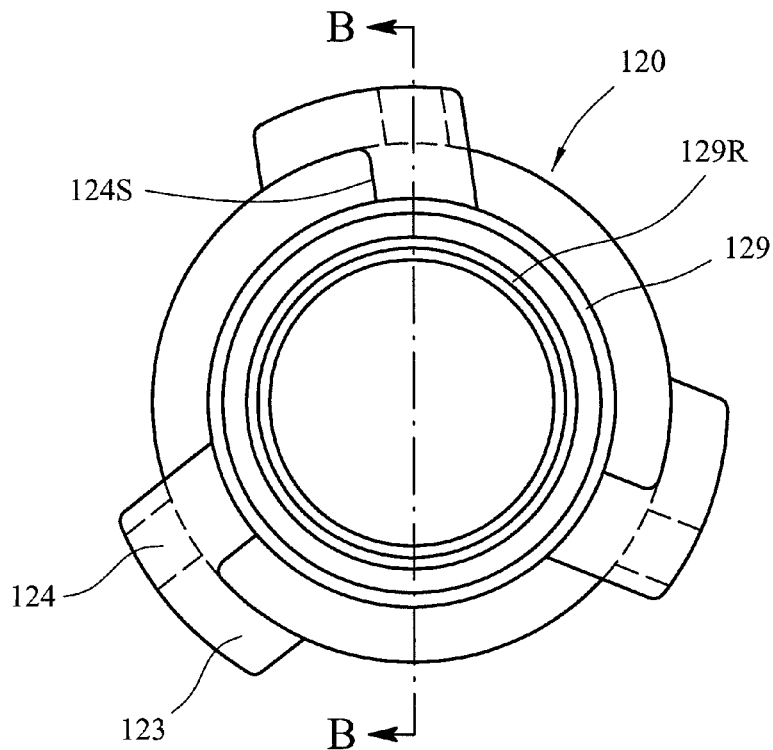
Figure 2D:
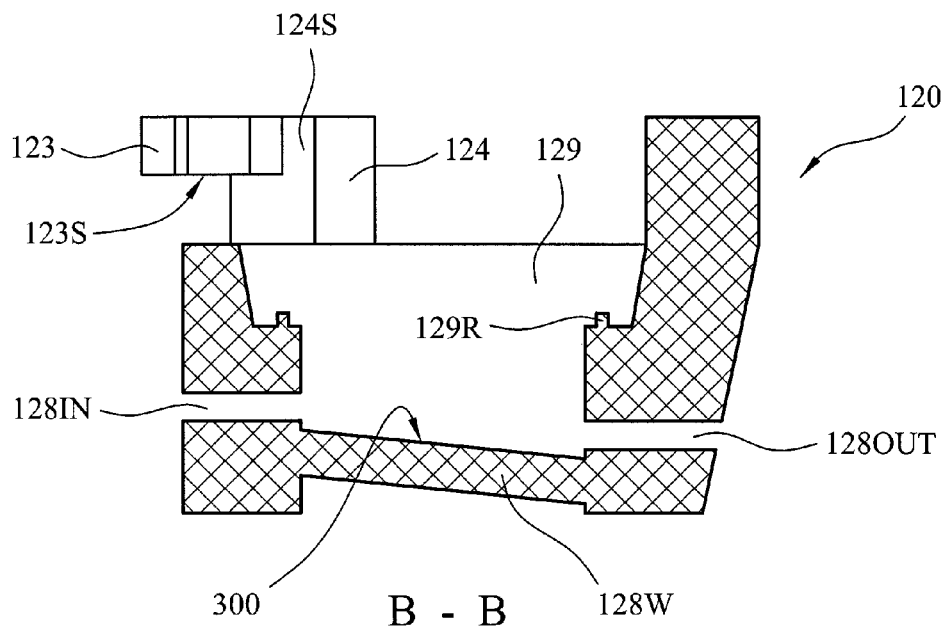
Figure 3:
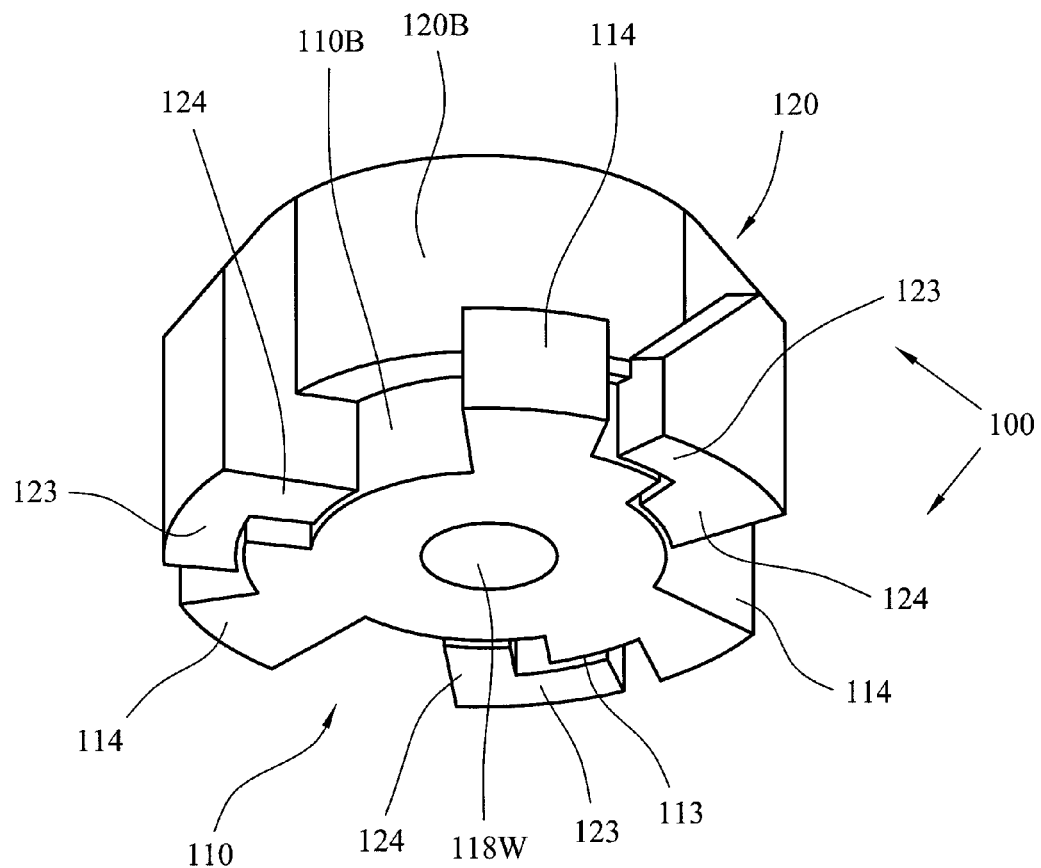
Figure 4:
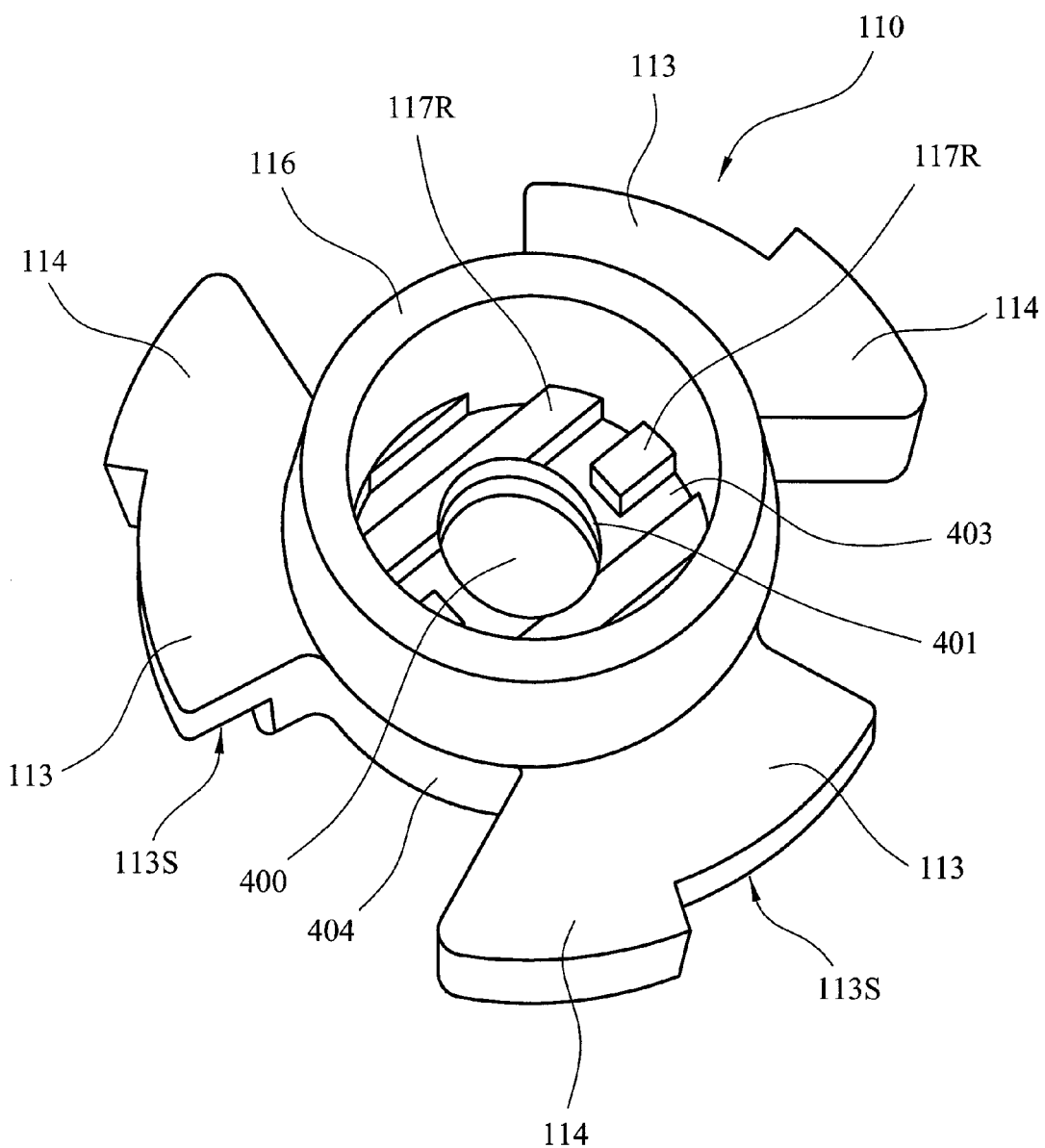
Figure 5:
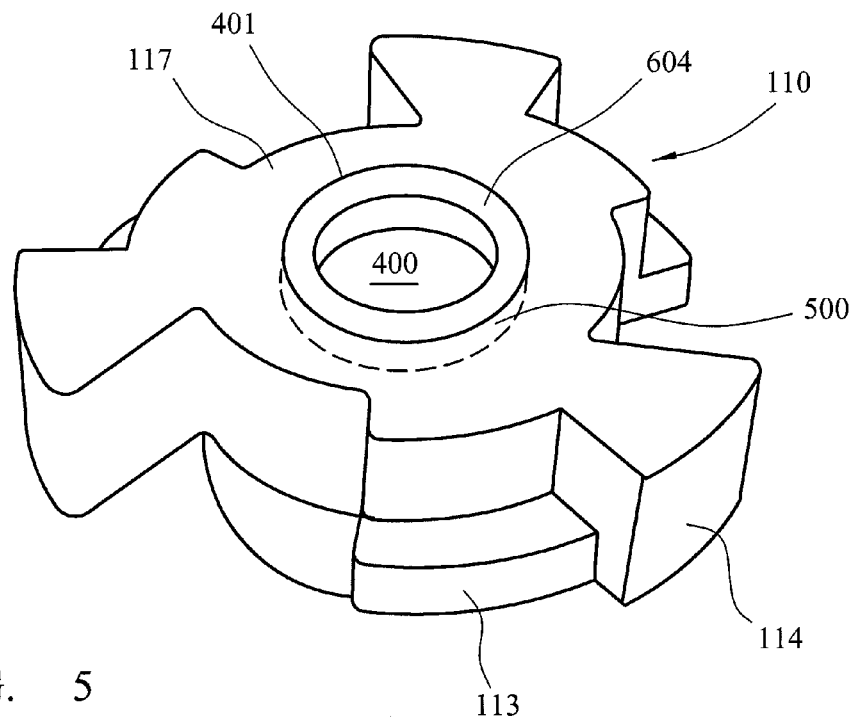
Figure 6:
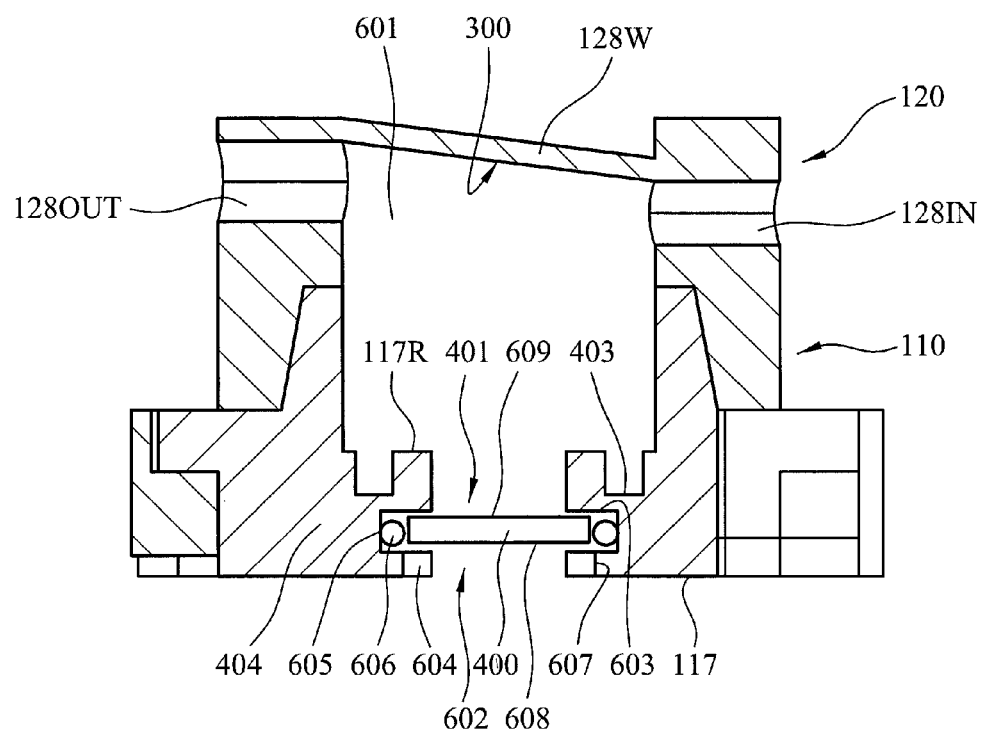
Figure 7:
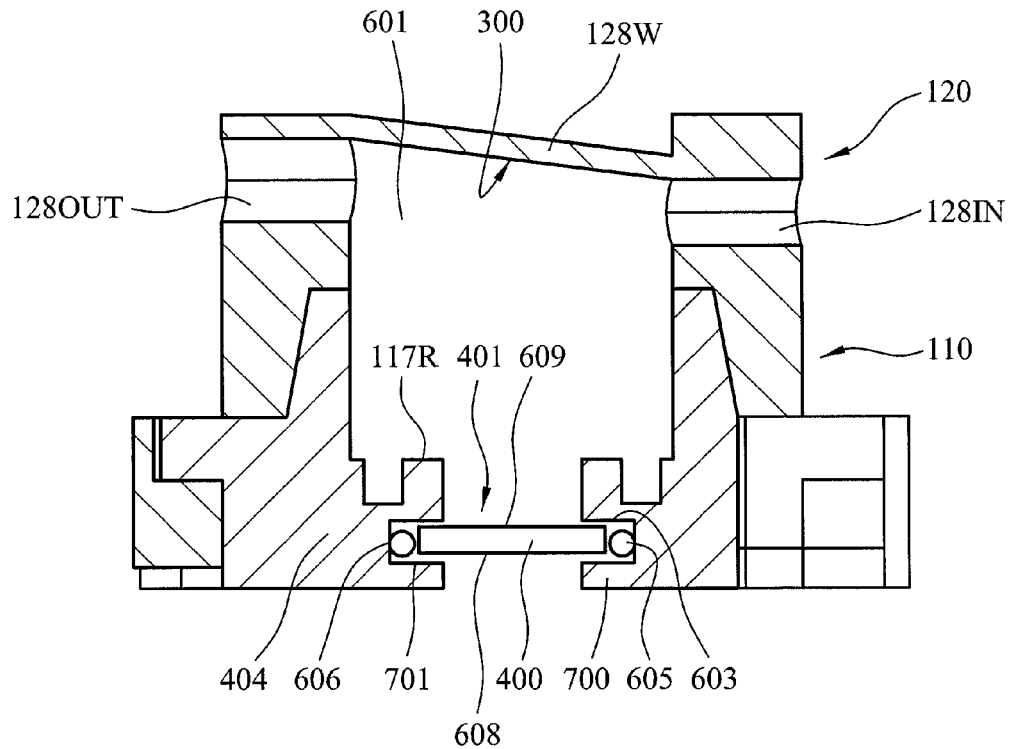
Figure 8:
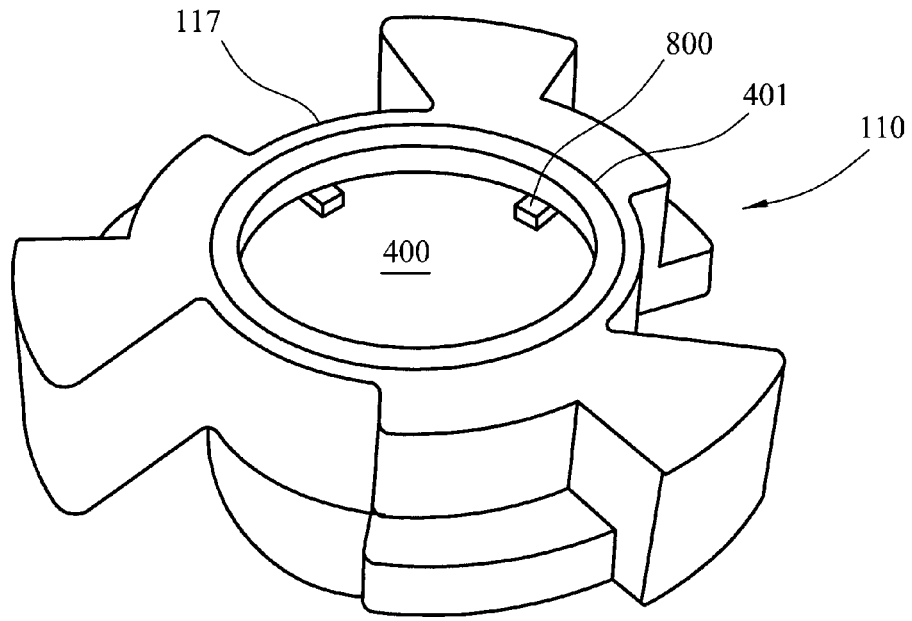
Figure 9:
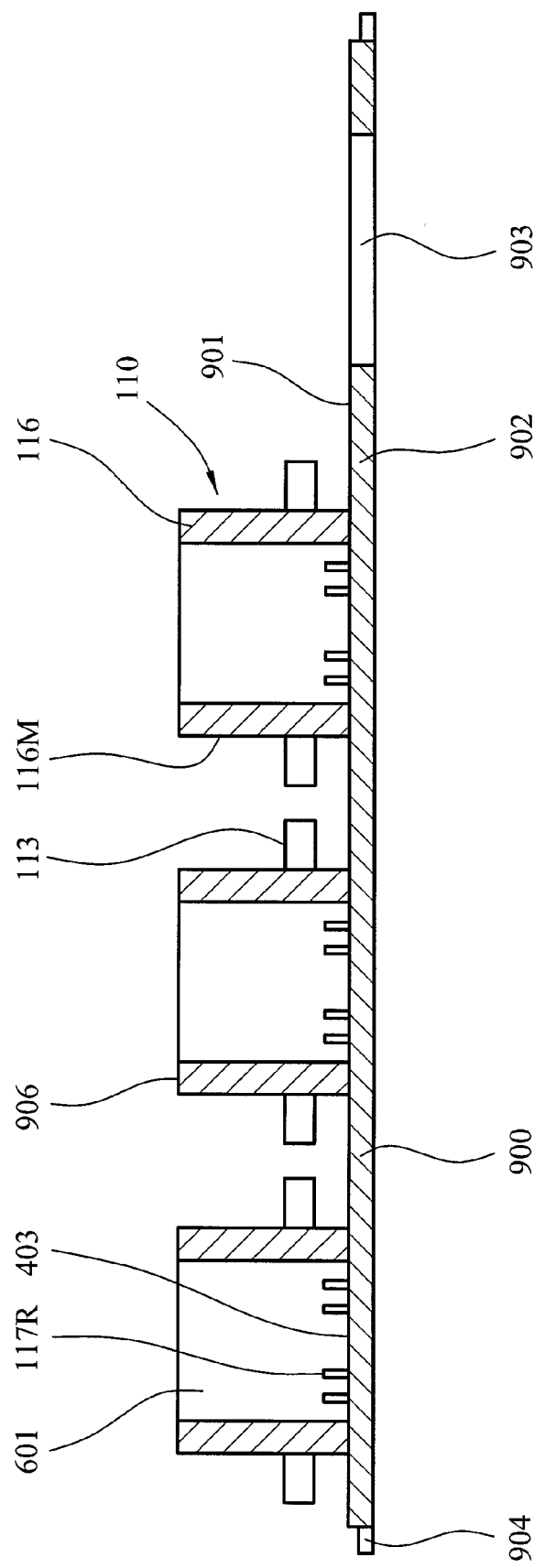
Figure 10:
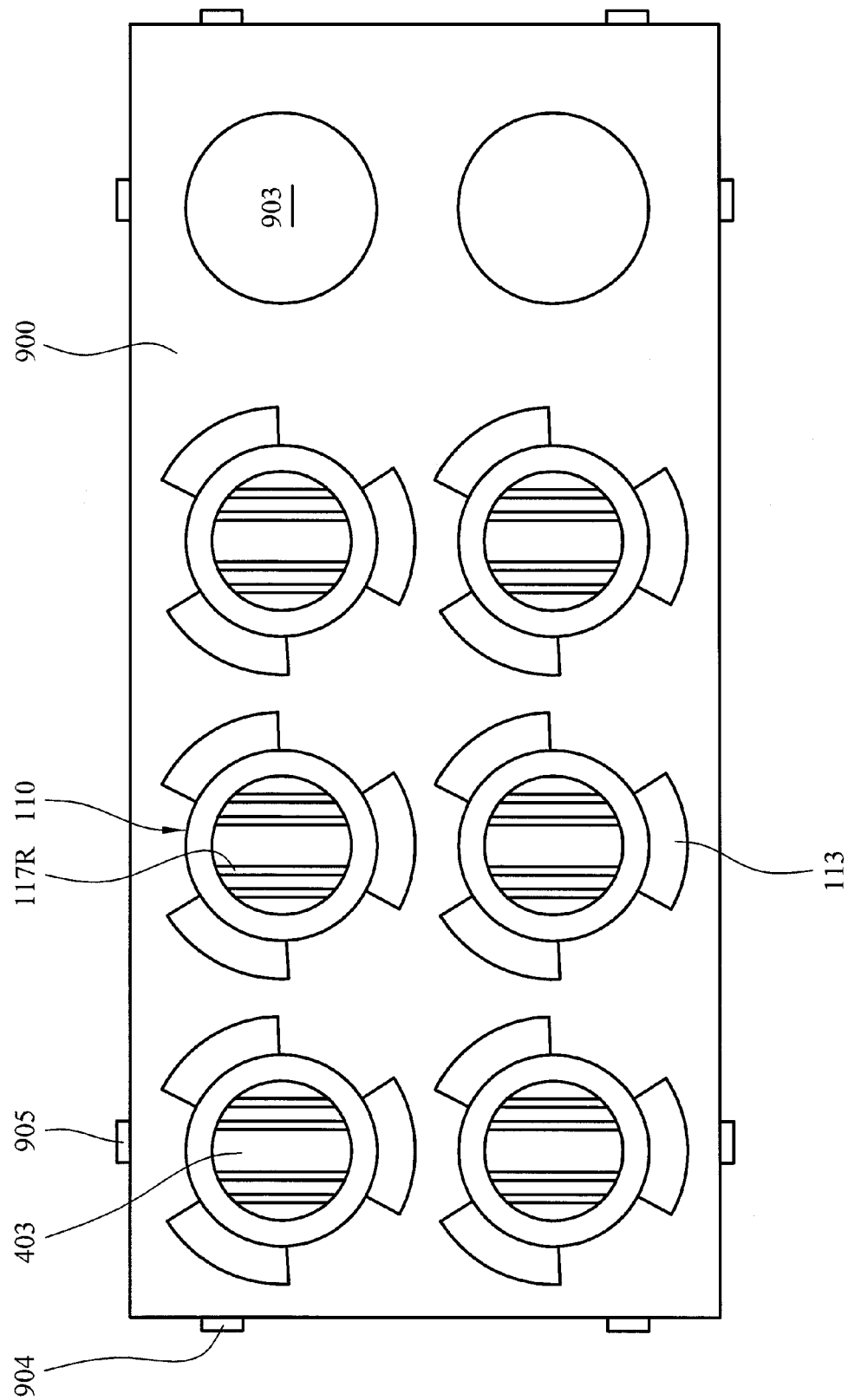
Figure 13:
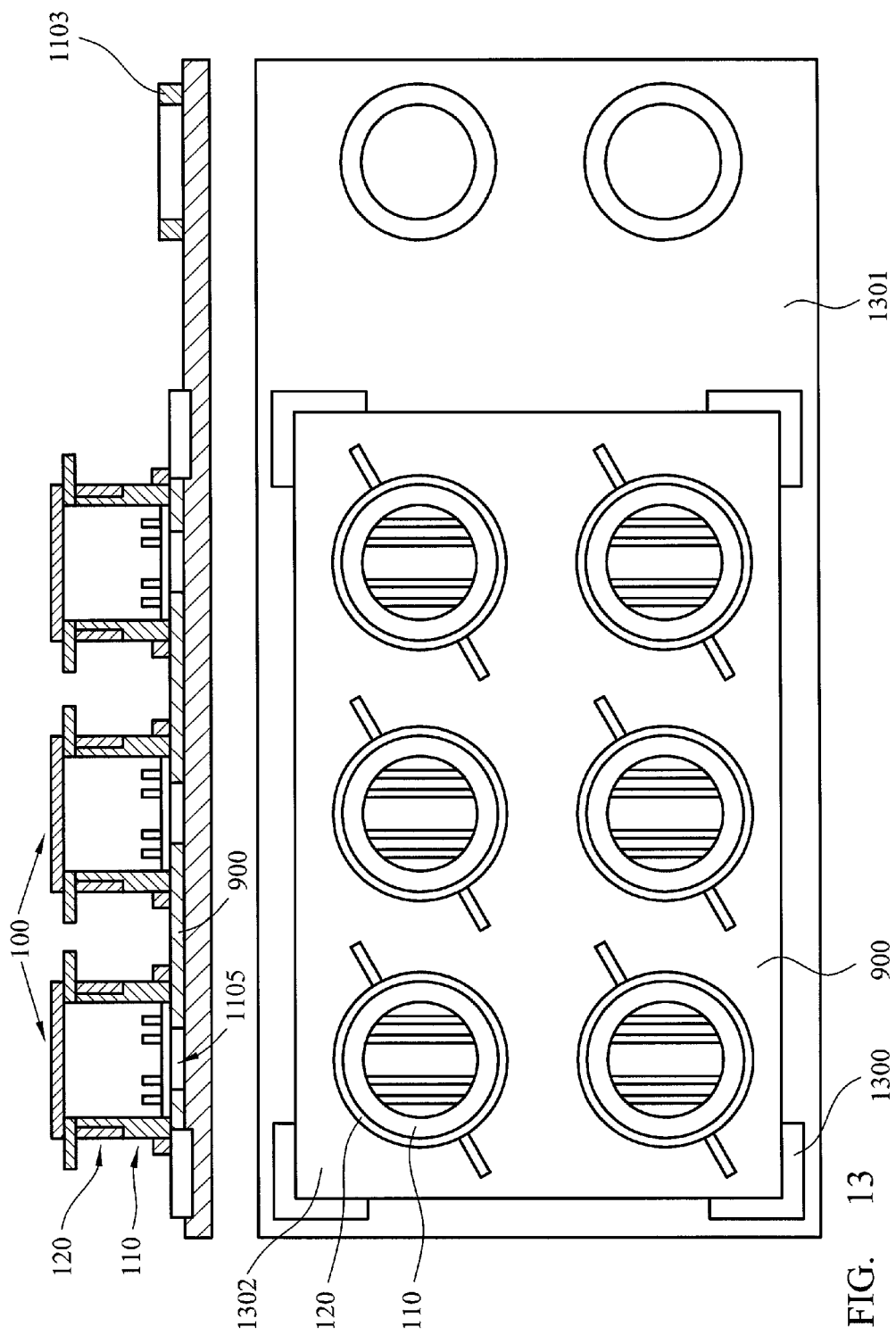

FIG. 2B a cross-sectional view along line A-A of the bioreactor base of FIG. 2A;

FIG. 2C is an underside view of the bioreactor cap part of FIG. 1C;

FIG. 2D a cross-sectional view along line B-B of the bioreactor cap of FIG. 2C;

FIG. 3 is a perspective view from below of the base part of FIG. 1B and the cap part of FIG. 1C of the bioreactor chamber assembled together to define in internal chamber;

FIG. 4 is a perspective top view of the bioreactor base of FIG. 1A and FIG. 1B having a viewing window formed from a separate piece of material according to a further specific implementation of the present invention;

FIG. 5 is a perspective underside view of the of the base of FIG. 4 showing the window insert in position at the bottom surface of the base;

FIG. 6 is a cross sectional side elevation view of the base and viewing window of FIG. 5;

FIG. 7 is a cross sectional side elevation view of a further embodiment of the base of FIG. 6 where the window piece is retained by the body of the base without a separate locating ring;

FIG. 8 is a perspective underside view of the base of FIG. 5 according to a further specific implementation;

FIG. 9 is a cross sectional side elevation view of a plurality of bioreactor base components arranged on a common support plate; and FIG. 10 is a top view of the multi-chamber plate arrangement of FIG. 9;

FIG. 11 is a cross sectional side elevation view of a plurality of bioreactors detachably mounted upon a common support plate and;

FIG. 12 is a top view of the multi-chamber plate arrangement of FIG. 11;

FIG. 13 is a top view of a further embodiment of the multi-chamber plate arrangement of FIG. 12.

FIGS. 1A to 4 illustrate components of a bioreactor chamber assembly 100 according to a specific embodiment of the present invention. The assembly 100 comprises a base component 110 as shown in FIGS. 1A and 1B 2 arranged to support the assembly 100 on a substantially flat horizontal surface such as a benchtop, and a cap component 120 as shown in FIG. 1C.

The base 110 has a substantially cylindrical basal portion 110B from which three support feet 114 protrude in a generally radial direction. The support feet 114 are spaced circumferentially about the basal portion 110B at intervals and are substantially equidistant from one another. The feet 114 are provided with flange portions 113 that protrude from the feet 114 in a common circumferential direction around the basal portion 110B. In the arrangement shown the flange portions protrude in an anticlockwise circumferential direction with respect to the view of FIG. 1A.

The flange portions 113 may be considered to be extensions of the feet 114 around the basal portion 110B, the flange portions being of a lower thickness in a direction parallel to an axis A of the body 110 normal to the radial and circumferential directions of the basal portion 110B. In the embodiment shown the flange portions 113 also extend a lesser radial distance away from the basal portion 110B than do the feet 114.

Each flange 113 comprises a thickness in the longitudinal direction of axis A that decreases in the circumferential direction away from foot 114. That is, when orientated in normal use, and upward facing surface of flange 113 is perpendicular to axis A whilst a lower downward facing surface 113S is inclined so as to be aligned transverse to a plane perpendicular to longitudinal axis A. This decreasing wedge shaped profile of flange 113 cooperates with a corresponding wedge shaped flange of cap component 120, discussed below, to progressively strengthen the fluid tight seal at the internal chamber. Abutment surface 113S terminates at a foot buffer surface 114S provided at foot 114.

It is to be appreciated that with the base 110 standing with the feet 114 on a flat surface a gap will exist between an underside of the flange portions 113 and the surface. This gap is arranged to be occupied by a portion of a flange 123 of the cap 120 when the body is coupled to the base 110 as described below.

The basal portion 110B of the base 110 has a substantially cylindrical mating portion 116 extending upwardly therefrom in an axial direction, a cylinder axis C of the mating portion coinciding with a longitudinal axis of the base 110 and of the chamber assembly. The mating portion 116 bears a mating surface 116M being a radially outer surface thereof. The mating portion 116 is tapered such that a thickness of the mating portion 116 decreases in a direction of the mating portion 116 away from the basal portion 110B, the mating portion 116 having an outer diameter that reduces with distance from the basal portion 110B.

An upper surface of the basal portion 110B facing upwardly along and within the mating portion 116 is provided with a specimen support 117 in the form of a plurality of ridged elements 117R. The ridged elements 117R are arranged to contact the specimen at spaced apart locations whereby a portion of a specimen suspended between the elements 117R is exposed to fluid within the mating portion 110. This feature reduces a risk of deterioration of a specimen due to restricted supply of nutrients, liquid, gas or any other required substance or medium. In some arrangements the specimen support 117 is arranged to support a specimen above the mating portion 116.

The cap component 120 has a body portion 120B having a substantially cylindrical outer wall 126. The body portion 120B is arranged to define an internal volume of the chamber assembly 100. At a first end 120B of the body portion 120B three arms 124 are provided at spaced apart locations around a circumference of the body portion 120B. The arms 124 project away from the body portion 120B in an axial direction. The arms 124 each have a flange portion 123 projecting from a lower edge thereof (with respect to a normal upright orientation of the body 120, which is opposite that shown in FIG. 1C). The flange portion 123 projects from the lower edge of each arm 124 in a substantially circumferential direction.

The arms 124 are spaced about the body portion 120B at locations corresponding to those of the feet 114 of the base 110. Accordingly, that the cap flange portions 124 are configured to cooperate with the base flange portions 113 to allow the base 110 and cap 120 to be coupled together. In use, the base 110 and cap 120 components are presented to one other and slid together such that the feet 114 and arms 124 of the respective components 110, 120 are substantially coplanar. The components 110, 120 are then twisted with respect to one another whereby the respective flange portions 113, 123 slide over one another via sliding contact between surfaces 113S and 123S until leading edges of each flange portion 113, 123 abut the respective alternative buffer surface 124S of arm 124 and buffer surface 114S of foot 114.

In particular, each flange 123 extending from arm 124 comprises a corresponding abutment surface 123S configured to abut surface 113S of face 110. As base flange 113 is tapered circumferentially such that it becomes progressively thicker in the axial direction towards foot 114, cap 120 and base 110 are drawn together in the axial direction as the abutment surfaces 113S, 123S slide in touching contact against one another. According to further embodiments, flange 123 may also comprise a tapering thickness in the circumferential direction about longitudinal axis A. Alternatively, flange 113 may comprise a uniform thickness in the axial direction whilst flange 123 comprises a wedged profile increasing in thickness in the axial direction towards arm 124.

In some embodiments the respective flange portions 113, 123 are arranged to provide a detente to reduce a risk of inadvertent separation of the components 110, 120.

An internal surface of the body portion 120B is provided with a mating surface 126M between the first end 120W and a shoulder 129 being a portion of the internal surface of the body portion 120B between the mating surface 126M and an inner sidewall 126I of the body portion 120B above the mating surface 126M. The inner sidewall 126I is oriented substantially parallel to the cylinder axis C of the cap 120 and is of a diameter smaller than that of the mating surface 126M at its vertically upper limit.

The mating surface 126M of the body portion 120B is arranged in use to abut the corresponding tapered cylindrical mating portion 116 of the base 110. A free end of the mating portion 116 of the base 110 is arranged to abut the shoulder 129 of the cap 120. In order to reduce a risk of fluid leakage from the assembly 100 the shoulder 129 is provided with a ridged portion 129R at a location substantially radially midway between opposed circumferential boundaries of the shoulder 129. Some embodiments are provided with a ridged portion 129R on the free end of the mating portion 116 instead of or in addition to the shoulder 129.

In the embodiment of FIG. 1A to 3, the base component 110 is provided with a window 118W in a lower surface thereof to allow inspection of a specimen supported on the ridge elements 117R. The window 118W may for example be used for visual inspection of the specimen, for example, using an inverted microscope and/or camera arrangement. Alternatively or in addition the window 118W may provide a port through which one or more other analytical instruments may inspect the specimen. In the embodiment of FIG. 1A to 3 the window 118W is recessed in a lower surface 117 of the basal portion 110B being a surface on which the base component 110 may be supported in use. The window 118W may be integrally formed with the base 110 or be a separate component connected to the base 110. In the embodiment shown the window 118W is integrally formed by moulding, the window being formed from the same material as the remainder of the base 110.

The presence of a specimen support having ridged elements 117R is advantageous in that it provides regions of the basal portion 110B of reduced thickness between the elements 117R allowing increased light transmission therethrough. Accordingly, an amount of light that may be transmitted from the specimen through the window 118W may be increased.

A fluid inlet aperture 128IN is provided through the body portion 120B of the cap component 120, the aperture being provided at a location of the body portion 120B such that the aperture 128IN is formed through the inner sidewall 126I above the mating surface 126M. A fluid outlet aperture 128OUT is provided through the body portion 120B at a location diametrically opposite the fluid inlet aperture 128IN and at substantially the same height above the first end 120B' of the body portion 120B in the longitudinal direction of axis A.

The cap component 120 also has a window 128W formed in an upper end surface or wall 127 thereof. Again the window 128W allows inspection of a specimen supported on the ridged elements 117R. Window 128W is integrally formed with the remainder of the cap 120 in a single moulding operation. Alternatively, window 128W may be formed non-integrally with cap 120 and is mounted via suitable mount means. Additionally, window 128W comprises a uniform thickness so as to eliminate any optical distortion when viewing the chamber interior.

In a preferred embodiment, an internal end 300 region of cap 120 that effectively defines the roof of the internal chamber comprises a taper or inclined surface. That is, the roof surface is aligned at an angle of approximately 8 degrees relative to a plane transverse to the longitudinal axis A. This sloping roof configuration allows air bubbles within the chamber interior to pass through the chamber and out of the outlet 128OUT. This is achieved as the outlet 128OUT is at a higher position than the inlet 128IN in the longitudinal direction of axis A when the cap 120 is orientated in normal use upon base 110 with outlet 128OUT positioned just below the upper end of the sloping internal chamber roof. According to the preferred embodiment, end region 300 is defined by transparent window 128W secured to cap 120 and having a uniform width across its diameter so provide the desired optical properties and facilitate viewing of the internal chamber without optical distortion.

According to further embodiments, the base component 110 and cap component 120 do not comprise respective windows 118W, 128W provided therein.

FIGS. 4 to 8 illustrate further embodiments of the base 110. Referring to the embodiment of FIGS. 4 to 6, base 110 comprises a viewing window 400 inserted into a base region 404 of base component 110. Window 400 is formed as a glass disc having excellent optical properties with regard to transparency such that a user may view the interior of the bioreactor chamber 601 from outside and below the bioreactor 602 as illustrated in FIG. 6. As indicated, window 400 is formed from a separate and different material to that of base 110. This allows optimisation of the optical properties of the window 400 without effecting the deformable and 'sealing' properties of base 110 and in particular the 'sealing' characteristics associated with mating surfaces 116M and 126M. As with the previous embodiment these surfaces are formed from silicone or a silicone based material or derivative. Window 400 is a silicone oxide based material and may comprise a coating provided on one or both circular surfaces and in particular surface 609 being upward facing into chamber interior 601. For example, the chamber facing surface 609 could be coated with a thin layer of silicone or other biologically inert material. Other coatings include anti-fouling or anti-adhesion coatings to inhibit biological or non-biological deposits adhering to surface 609 and impairing optical transparency when viewed from below 602.

According to the embodiment of FIGS. 4 to 6, glass disc 400 is located within the lower region 404 of base 110 within a recessed disc-shaped socket 605 having a diameter slightly greater than the diameter of disc 400. An o-ring 606 or other suitable seal is positioned circumferentially around disc 400 within socket 605 to provide a fluid tight seal at the lower region 404 and socket 605. Disc 400 and seal 606 are retained in position within socket 605 by a circular inner shoulder 603 of base 101 that abuts against a perimeter region of chamber facing surface 609. A second shoulder 607 at region 404 of base 101 extends towards a perimeter region of an external facing surface 608 of window 400. According to the specific embodiment, disc 400 is securely held in position by an annular retainer 604 that is mated with shoulder 607 via screw threads 500 or a fiction fit components including for example straight or tapered mating surfaces of shoulder 607 and retainer 604. Accordingly, window 400 may be removed and cleaned by screwing or unclipping retainer 604 from its mounting location adjacent base shoulder 607.

Window 400 is located below a lower surface 403 of internal chamber 601 and below the ridged elements 117R when the base is orientated in normal use. Accordingly, window 400 does not interfere with the specimen or specimen support mounted upon elements 117R. Window 400 bridges the central aperture 401 extending through the lower region 404 of base 110 and is positioned directly below the specimen and specimen support mounted upon elements 117R.

FIG. 7 illustrates a further embodiment of the base of FIG. 6. In this arrangement, the disc-like window 400 is retained in position at base region 404 exclusively by the body of base 110 at the region of socket 605. That is, as the base 110 is formed from silicone or a silicone based material, it is deformable such that window 400 may be manipulated into socket 605 via a user bending and/or twisting the base region 404. According to the further embodiment, the lower (external facing) circular shoulder 700 of socket 605 comprises a smaller diameter than the diameter of window 400 so as to abut against the perimeter region of external facing surface 608. As before, window 400 is prevented from displacement inwardly (towards chamber interior 601) by circular shoulder 603. The same o-ring seal 606 extends around the perimeter of disc 400 so as to provide a fluid tight seal at the aperture 401 across which window 400 extends.

FIG. 8 illustrates a further embodiment of the base of FIGS. 6 and 7. In this arrangement, the disc-like window 400 comprises a diameter approximately equal to the internal diameter of chamber 601 such that the entire contents of the chamber 601 may be viewed from below 602. Specimen supports 800 extend radially inward from the side walls that define internal chamber 601 at base 110 and are configured for mounting the specimen at the lower region of base 110 being identical in function to ridge elements 117R. According to the embodiment of FIG. 8, disc 400 is retained in position without the use of a retainer 604 and is accommodated within the same recessed socket 605 and abutment shoulders 603, 700 described with reference to FIG. 7.

FIGS. 9 and 10 illustrate a further embodiment of the present invention in which a plurality of base components 110 are mounted and extend from a common support plate 900. Support plate 900 is substantially planar and comprises a rectangular configuration having a lower surface 902 and an upper surface 901 from which extend the plurality of base components 110. According to the specific implementation, each base 110 and the plate 900 are formed integrally and comprise a transparent polymer based material such as a thermoplastic and in particular an acrylic or a polycarbonate. The bases 110 and plate 900 may also comprise silicone and in particular silicone rubber being the same material as cap 120. Whilst it is preferred that the entire assembly comprising bases 110 and plate 904 are formed integrally, via a conventional moulding and in particular injection moulding process, each base 110 may be formed non-integrally with base 900 and may be attached together using suitable attachment means. For example, each base 110 may be permanently or released secured to plate 900 using an adhesive, heat treatment and/or a mechanical lock mechanism including frictional fit arrangements or separate additional locking components (not shown) provided on both base 110 and plate 900 that may be mated together to lock each base 110 at plate 900.

The preferred construction method is to form the base and plate assembly integrally via an injection moulding process. Each base 110 comprises the same or very similar configuration to those base components 110 described with reference to FIGS. 1A to 3 or 4 to 8. As the base plate 900 is formed from a thermoplastic material having excellent transparency this obviates the need for a separate window insert 400 described with reference to FIGS. 4 to 8. Ridge elements 117R extend upwardly from upper surface 901 of plate 900 at region 403 within base 110 that, in part, defines internal chamber 601.

Accordingly, a specimen support, as described with reference to FIGS. 1 to 8 may be mounted upon elements 117R within chamber interior 601 immediately above surface 403. As the entire plate 900 is formed from a transparent thermoplastic material, the entire interior 601 of the bioreactor 100 may be viewed preferably from below lower surface 902. As the plate 900 is substantially planar, a microscope (not shown) may be positioned in very close proximity to the specimen support mounted upon elements 117R. This is advantageous for imaging clarity. Also, the microscope and/or the plate 900 may be moved conveniently between biochambers 100 via mounting upon common support plate 900. Additionally, as each base 110 is formed from the transparent thermoplastic material, the chamber interior 601 may also be viewed from the side.

Each base 110 comprises the same locking flanges 113 configured to interengage with locking flanges 123 of the biochamber cap or upper body component 120 described with reference to FIGS. 1 to 3. The thermoplastic bases 110 of FIGS. 9 and 10 are each independently capable of mating and locking with respective cap components 120 so as to complete each biochamber 100 extending from common support plate 900. As the cap component 120 comprises the deformable silicone material a suitable fluid tight seal is provided between the thermoplastic mating surface 116M of base 110 and the silicone surface 126M of cap 120. As described with reference to FIGS. 1 to 3, cap 120 may also comprise an additional sealing ridge 129R configured to mate with the end region 906 of tapered mating portion 116 as the cap 120 and base 110 are mated together via locking flanges 113, 123.

Base plate 900 further comprises apertures 903 to accommodate suitable fluid reservoir bottles (not shown) containing the fluid for circulation between the chambers 100. As each cap 120 may be independently secured to each base 110, a user may conveniently configure the tubing interconnections extending from the fluid inlet and outlets 128IN, 128OUT as desired and described with reference to FIG. 1. That is, each chamber 100 mounted at plate 900 may be interconnected with neighbouring chambers 100 in series, in parallel or independently to specific fluid reservoirs (not shown).

Plate 900 further comprises a set of end connectors 904 and side connectors 905. Connectors 904, 905 enable a plurality of plates 900 to be releasably connected together to form an array, each plate comprising a plurality of chambers 100 formed from base component 110 and cap component 120.

According to a further embodiment, plate 900 may comprise a material that is not transparent. Accordingly, a separate window insert similar to the window 400 described with reference to FIGS. 4 to 8 may be secured at regions 403 of plate 900 to enable a user to view chamber interior 601.

FIGS. 11 and 12 illustrate a further embodiment of the present invention in which a plurality of bioreactors are detachably mounted at a common support plate or tray 900. Support tray 900 comprises a plurality of apertures 1105 extending through the entire thickness of tray 900 from upper surface 901 to lower surface 902. Each individual bioreactor is positioned over and about each aperture 1105 extending upwardly from upper surface 901.

According to the specific implementation, each bioreactor comprises a substantially cylindrical geometry and each aperture 1105 is circular wherein a diameter of each aperture 1105 is less than a diameter of the internal chamber of each bioreactor, when viewed in plan, such that a lip 1109 extends inwardly beyond the upstanding walls 1110 of each bioreactor. Lip 1109 is of a sufficient depth to support transparent window 400 that comprises a diameter corresponding to that of the internal chamber of each bioreactor and being greater than the diameter of each aperture 1105. Each window 400 may be detachably or permanently attached to each bioreactor base 110 using suitable attachment means. Window 400 therefore defines the support for the specimen via ridged elements 117R.

Tray 900 comprises a plurality of shoulders 1104 extending upwardly from upper surface 901. The shoulders 1104 are positioned at the region of each aperture 1105 and are dimensioned and relatively positioned so as to abut against the outer surface of each bioreactor wall 1110 when each bioreactor is respectively positioned at tray 900 above each aperture 1105. According to a specific implementation, each shoulder 1104 comprises an internal facing surface 1106 relative to each bioreactor with each surface 1106 comprising one half of a releasable locking mechanism configured to releaseably mate with a second part of the locking mechanism formed on the external facing surface 1107 of each bioreactor base 110. This releasable locking mechanism may comprise a click-lock mechanism, a twist-lock mechanism, a bayonet arrangement, cooperating screw threads, a push-fit arrangement, a snap-lock arrangement or any friction fit releasable locking mechanism having a first part provided at each shoulder 1104 and a second part provided at each bioreactor base 110. According to further embodiments, the upper surface 901 of tray 900 may comprise a recessed portion to receive a lower region of each wall 1110 of bioreactor base 110 so as to releaseably lock each bioreactor in position at tray 900.

Tray 900 also comprises bottle and peristaltic pump holder regions 1102 defined by short cylindrical walls 1103 so as to define an open topped trough into which a fluid reservoir bottle or pump may be introduced and held by the frictional contact with the internal facing surface of surrounding retaining walls 1103.

As detailed previously, each bioreactor comprises a base 110 and a cap 120 releaseably secured together to define an internal chamber 601. According to the further embodiment, both the cap 120 and base 110 comprise cooperating screw threads to allow cap 120 to be interlocked with base 110 via corporation of the screw type interlocking mechanism. In particular, a first part of a screw interlocking mechanism is provided on an upper region 1100 of the external facing surface of walls 1110. Accordingly, a second part of the screw interlocking mechanism is formed on a lower region 1108 of an internal facing surface of cap 120 that is capable of interfacing with the external facing region 1100 of base 110. Radially extending arms 1101 project radially outward from cap 120 at diametrically opposed regions. Arms 1101 are of a sufficient length so as to be manipulated by the thumb and fingers of a user to twist lock cap 120 onto base 110 to define bioreactor internal chamber 601.

As detailed with reference to FIG. 1A to 8, at least one of the mating surfaces of the base 110 and cap 120 comprises a tapered portion. Optionally, both of the mating surfaces of the base 110 and cap 120 comprise surfaces that are tapered in a complimentary manner so as to provide a hygienic fluid-type seal when both the base 110 and cap 120 are locked together as described. The further embodiment of FIGS. 9 to 12 may also comprise the ridged portion 129 that further helps with the provision of a fluid-type seal at internal chamber 601.

According to the further embodiment of FIGS. 11 and 12, tray 900 may comprise a material that is not transparent or translucent as the chamber interior 601 may be viewed through transparent window 400 extending over apertures 1105. Additionally, the further embodiment of FIGS. 11 and 12 may further comprise the set of end 904 and side 905 connectors as described with reference to FIGS. 9 and 10.

FIG. 13 illustrates a further embodiment of the multi chamber and tray assembly of FIG. 12. According to the further embodiment, tray 900 comprises a reduced length and possibly width to the embodiment of FIG. 12. The tray 900 is appropriately sized to clip within a larger tray holder 1301. Typically, tray 900 comprises a 127.9 mm length and a 85.6 mm width. Unlike the embodiment of FIG. 12, holder 1301 comprises the bottle and peristaltic pump holder regions 1102 positioned spaced apart from the array of bioreactors 100. A width of holder 1301 is slightly larger than tray 900 such that tray 900 sits within the perimeter of holder 1301. Four mountings 1300 are provided at holder 1301 and are spaced apart and positioned so as to correspond to the four corners 1302 of the smaller tray 900. Accordingly, tray 900 may be removably clipped in position within mountings 1300 so as to be releasably attached to support 1301. The respective edge surfaces at corners 1302 that are positioned opposed to mountings 1300 maybe configured to comprise one half of a releasable locking mechanism configured to releasably mate tray 900 at holder 1301 with the second half of the mechanism provided at the inner facing surfaces of mountings 1300.

The arrangement of FIG. 13 enables the bioreactor multi chamber apparatus to be conveniently attached and released from a suitable mount 1301 of appropriate size for installation within different types of biological processing and analysis apparatus including microscopes and incubators etc.

According to the embodiments of FIGS. 12 and 13, the bases 110 and caps 120 are injection moulded using a material of Medical Grade USP Class VI and the tray is thermoformed. The material of tray 900 is also preferably medical grade.

The invention claimed is:

1. A bioreactor chamber assembly comprising:
   a base and a cap configured to be coupled together to define an internal chamber;
   the base and cap each comprising a plurality of respective interengaging flanges to allow the base and cap to be releasably coupled together axially relative to a longitudinal axis bisecting the base and cap by rotation of at least one of the base and cap about the longitudinal axis;
   the flanges at each of the base and cap being respectively spaced apart in a direction around the longitudinal axis by gap regions configured to be occupied by at least a portion of the flange of the respective opposing base or cap, each flange having an abutment surface extending radially relative to the axis, the abutment surfaces at the base configured to slide over the abutment surfaces at the cap in touching contact by rotation of at least one of the base and cap about the axis such that at least a part of the flange of the base and the flange of the cap overlap in the axial direction to couple and lock the base and cap axially relative to one another;
   wherein each flange of the abutment surfaces extends in a circumferential direction around the longitudinal axis;
   wherein at least one of the abutment surfaces extends in a circumferential direction at an angle transverse to a plane perpendicular to the longitudinal axis such that as the flanges of the base and the flanges of the cap are slid over one another the base and cap are drawn together axially,
   wherein the respective interengaging flanges project radially outward from both the base and cap.

2. The assembly as claimed in claim 1, wherein the respective interengaging flanges are spaced apart circumferentially around the base and cap.

3. The assembly as claimed in claim 1, wherein the respective interengaging flanges each comprise a portion extending in the circumferential direction around the base and cap wherein the respective flange portions of the base and cap are configured to slide over one another to couple the base and cap together and prevent axial separation.

4. The assembly as claimed in claim 1, wherein the base and cap each comprise a respective sealing surface that may be drawn and mated together axially via an interference fit arrangement by said rotation and the contact between the abutment surfaces to provide a fluid tight seal when the base and cap are locked together axially.

5. The assembly as claimed in claim 4, wherein at least one of the sealing surfaces extends in the direction of the longitudinal axis and is tapered to extend transverse to the longitudinal axis so as to provide the interference fit arrangement with the corresponding sealing surface of the base or cap.

6. The assembly as claimed in claim 4, wherein at least one of the sealing surfaces of the base and cap comprises a ridged portion extending circumferentially around the internal chamber to abut against a portion of the sealing surface of the alternate base or cap to provide a fluid tight seal.

7. The assembly as claimed in claim 1, wherein the interengaging flanges of the base and cap are formed integrally with the respective base and cap.

8. The assembly as claimed in claim 1, wherein the cap comprises a fluid inlet aperture and a fluid outlet aperture.

9. The assembly as claimed in claim 1, wherein at least one of the cap and base comprise side walls that extend in the direction of the longitudinal axis that define a part of the internal chamber.

10. The assembly as claimed in claim 1, wherein at least a portion of at least one of the base and cap comprises a resilient deformable material.

11. The assembly as claimed in claim 10, wherein the resilient deformable material comprises silicone.

12. The assembly as claimed in claim 11, wherein the base and cap comprise predominantly silicone.

13. The assembly as claimed in claim 1, wherein the base comprises a transparent window non-integrally formed with the base.

14. The assembly as claimed in claim 13, wherein the base comprises a receiving socket extending around an aperture at an end region of the base, the window partially received by the socket to retain the window at the base.

15. Bioreactor apparatus comprising:
   a plurality of bioreactor chamber assemblies as claimed in claim 1; and
   a support structure mounting the plurality of the bioreactor chamber assemblies in substantially fixed position at the support structure, the support structure comprising a plurality of respective mounts to releasably mount each bioreactor chamber assembly at the support structure via the base of each bioreactor chamber assembly.

16. The apparatus as claimed in claim 15, wherein the support structure comprises a plurality of apertures, each aperture provided at a region of each respective mount such that each respective aperture is positioned below a respective bioreactor chamber assembly when mounted at the support structure.

17. The apparatus as claimed in claim 15, wherein the mount comprises at least one shoulder extending upwardly from the support structure to abut against an outer surface of each respective base.

18. A method of creating and maintaining an environment to support a biological species, the method comprising:
   providing a chamber body having walls that define an internal chamber to accommodate the biological species;
   the chamber body comprising:
   a base and a cap configured to be coupled together to define the internal chamber;
   the base and cap each comprising a plurality of respective interengaging flanges to allow the base and cap to be releasably coupled together axially relative to a longitudinal axis bisecting the base and cap by rotation of at least one of the base and cap about the longitudinal axis;
   the flanges at each of the base and cap being respectively spaced apart in a direction around the longitudinal axis by gap regions configured to be occupied by at least a portion of the flange of the respective opposing base or cap, each flange having an abutment surface extending radially relative to the axis, the abutment surfaces at the base configured to slide over the abutment surfaces at the cap in touching contact by rotation of at least one of the base and cap about the axis such that at least a part of the flange of the base and cap overlap in the axial direction to couple and lock the base and cap axially relative to one another;

wherein each flange of the abutment surfaces extends in the circumferential direction around the longitudinal axis;

wherein at least one of the abutment surfaces extends in a circumferential direction at an angle transverse to a plane perpendicular to the longitudinal axis such that as the flanges of the base and cap are slid over one another the base and cap are drawn together axially, wherein the respective interengaging flanges project radially outward from both the base and cap; and providing a flow of a liquid through the internal chamber in contact with biological species via a liquid inlet and a liquid outlet at the chamber body.

19. The method according to claim 18, wherein the base and cap each comprise a respective sealing surface that may be drawn and mated together axially via an interference fit arrangement by said rotation and the contact between the abutment surfaces to provide a fluid tight seal when the base and cap are locked together axially.

* * * * *